United States Patent

Van Driel et al.

Patent Number: 5,811,658
Date of Patent: Sep. 22, 1998

[54] ULTRASONIC DIVERSION OF MICROAIR IN BLOOD

[75] Inventors: Michael R. Van Driel, Fountain Valley; Jorge Jeffery, South Gate; Yu-Tung Wong, Huntington Beach, all of Calif.

[73] Assignee: Medtronic, Inc., Minneapolis, Minn.

[21] Appl. No.: 840,686

[22] Filed: Apr. 29, 1997

[51] Int. Cl.⁶ .......................... G01N 30/02; G01N 30/09
[52] U.S. Cl. .................................................. 73/19.02
[58] Field of Search .................. 128/662.02, 662.06, 128/DIG. 12, DIG. 13; 604/19, 122; 210/748, 645; 73/19.03, 19.12

[56] References Cited

U.S. PATENT DOCUMENTS

| | | | |
|---|---|---|---|
| 3,974,681 | 8/1976 | Namery | 128/DIG. 13 X |
| 4,565,500 | 1/1986 | Jeensalute et al. | 128/DIG. 13 X |
| 5,103,827 | 4/1992 | Smith | 128/DIG. 13 X |
| 5,357,781 | 10/1994 | Tikijian | 73/19.12 X |
| 5,394,732 | 3/1995 | Johnson et al. | 73/19.03 X |
| 5,447,052 | 9/1995 | Delaune et al. | 73/19.12 X |
| 5,503,801 | 4/1996 | Brugger | 210/645 X |
| 5,515,713 | 5/1996 | Saugues et al. | 73/19.03 |
| 5,591,251 | 1/1997 | Brugger | 604/122 X |

FOREIGN PATENT DOCUMENTS

| | | |
|---|---|---|
| 1173302 | 8/1985 | U.S.S.R. |
| 1620931 | 1/1991 | U.S.S.R. |

*Primary Examiner*—William L. Oen
*Attorney, Agent, or Firm*—Harry G. Weissenberger

[57] ABSTRACT

Microair bubbles in a bloodstream are diverted from the bloodstream in a diversion chamber by ultrasonic energy, and are collected in a blood-filled stasis column where they can be accurately measured by a bubble detector and then vented to atmosphere. Bubbles of different sizes can be separated into different stasis columns for enhanced measurement.

6 Claims, 1 Drawing Sheet

ULTRASONIC DIVERSION OF MICROAIR IN BLOOD

FIELD OF THE INVENTION

This invention relates to the handling of microair bubbles in blood, and more specifically to a system which uses ultrasound to separate and sort microair bubbles in a flowing bloodstream for treatment appropriate to their size.

BACKGROUND OF THE INVENTION

During open-heart surgery, microscopic air bubbles having a diameter on the order of 60–300 $\mu$m are frequently entrained into the blood circuit of the heart-lung machine in spite of careful defoaming of the blood passing through the machine. The larger sizes of these microair bubbles have been suspected of causing memory loss, strokes and other undesirable effects in the patient. Filtration of the defoamed blood is not always effective. A filter can only stop bubbles larger than its pore size. Over time, the filter will tend to break down, and previously trapped bubbles will escape from the filter. Previously trapped bubbles may start as very small emboli, but they can combine to form much larger emboli later when they escape. Furthermore, a filter involves intimate physical contact between the filter material and the blood, which is a potential source of contamination and hemolysis.

To combat the problem of air emboli, it has previously been proposed to monitor the bloodstream through the heart-lung machine with ultrasound equipment capable of detecting the passage of a bubble in the stream. Unfortunately, the best that detection can do is to warn the perfusionist, who must then evaluate the problem and, if necessary, take remedial measures that may interrupt the surgery. Also, echo-locating and sizing air bubbles in a bloodstream requires rather sophisticated and expensive analytical electronics to interpret the ultrasonic echo signal.

A device using acoustic energy to separate small microair bubbles from a moving bloodstream was disclosed in the article "The acoustic filter: An ultrasonic blood filter for the heart-lung machine" by Schwarz et al. published at pp. 1647–1653 of the December 1992 issue of *The Journal of Thoracic and Cardiovascular Surgery*. In that article, a high-intensity ultrasound transducer operating at 1 MHz in a water bath directed ultrasound energy into an elongated horizontal manifold through which a bloodstream containing microair bubbles with diameters on the order of 4–32 $\mu$m was conveyed in a downward direction. The microair bubbles were diverted out of the bloodstream by the acoustic energy and were collected in an upwardly directed secondary blood flow at a location spaced from the main bloodstream. The secondary blood flow was then recycled through the defoamer/filter.

Neither of the above-described prior art devices was practical to use, however, for the dual purpose of eliminating microbubbles completely from a heart-lung machine blood circuit while measuring their size and quantity so as to provide information from which the perfusionist can identify trouble spots in the circuit.

SUMMARY OF THE INVENTION

The present invention allows the elimination of microair bubbles from a moving bloodstream without loss or diversion of blood, and without losing efficiency over time, by using acoustic radiation, e.g. ultrasonic energy, to push acoustically active particles such as air bubbles transversely to the main bloodstream into a stasis area where they can be easily measured and, from which they can be removed without interfering with the main bloodstream. The resulting diversion of the bubbles thus provides in effect, a contactless filtration of the main bloodstream while at the same time providing valuable bubble size and quantity information.

DESCRIPTION OF THE PREFERRED EMBODIMENTS

Figure 1:
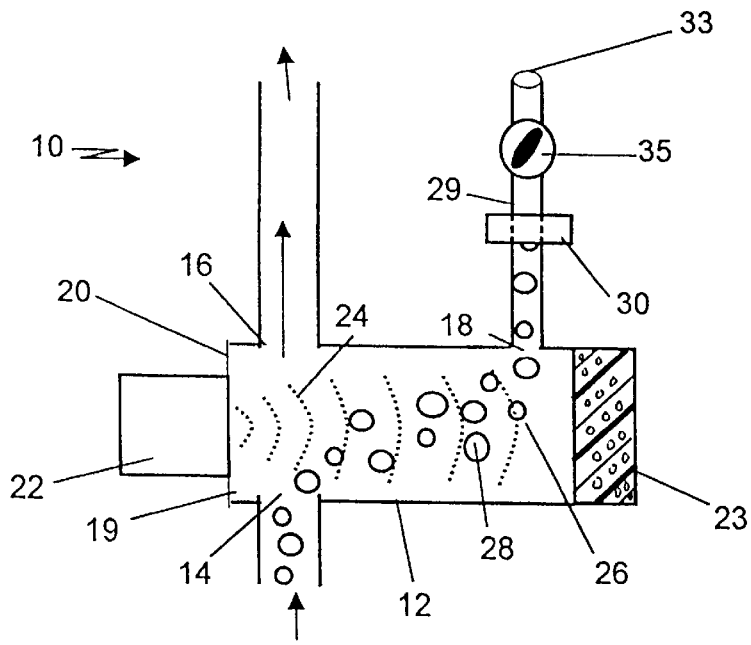
FIG. 1 is a vertical section, partly in schematic form, of a first embodiment of the invention.

FIG. 1 illustrates a first preferred embodiment of the acoustic filter 10 of this invention. A diversion chamber 12 has a blood inlet 14 at its bottom, a main blood outlet 16 at its top in substantial axial alignment with the inlet 14, and a secondary blood outlet 18 at its top in a position laterally spaced from the inlet 14 and outlet 16. The chamber 12 may be of any convenient shape such as a laterally extending tube of hard plastic material.

The open lateral end 19 of the chamber 12 is closed off by a thin, flexible mylar sheet 20. An ultrasound transducer 22 is mounted in intimate acoustic contact with the mylar sheet 20 by the interposition of an appropriate conventional acoustic gel (not shown) between the transducer 22 and the mylar sheet 20. The other end of the chamber 12 is closed off by an acoustically absorbent but blood-impervious material such as a biologically inert plastic foam 23.

In use, blood flows upwardly from inlet 14 to main outlet 16 through the blood-filled chamber 12. As the bloodstream passes the transducer 22, acoustic radiation (symbolically represented by lines 24 in FIG. 1) is transmitted in a direction transverse to the bloodstream from the transducer 22 through the mylar sheet 20. In a preferred embodiment of the invention, the transducer may operate at a frequency of about 1 MHz with a power level of about 20 W.

The acoustic radiation 24 impinging upon acoustically active particles such as air bubbles impels them in a lateral direction away from the transducer 22. The action of the acoustic radiation 24 is much stronger on smaller microair bubbles 26 than on larger bubbles 28, although both are sufficiently diverted from the main bloodstream to enter into the stasis column 29 connected to outlet 18. The bubbles exiting the chamber 12 through the outlet 18 rise relatively slowly in the stasis column 29 because the blood in column 29 does not flow. This greatly enhances the ease and accuracy of counting and sizing them. The counting and sizing is done by a suitable detector 30, which may be a device of the type described in more detail in our copending application Ser. No. 08/841,015 filed 29 Apr. 1997. Accumulated air can be vented, if necessary, from the stasis column 29 through vent 33 by opening the stopcock 35. The main bloodstream exiting the chamber 12 through outlet 16 is free of bubbles and has thereby been effectively filtered without physical contact between the blood and a filter medium. Also, it will be noted that because the bubbles 26, 28 are diverted into a stasis area, no blood volume is lost from the bloodstream as would be the case if the bubble-containing portion of the blood were recycled or otherwise processed. Consequently, the appearance of troublesome bubbles does not require any shutdown or adjustment of the blood circuit of the heart-lung machine.

Figure 2:
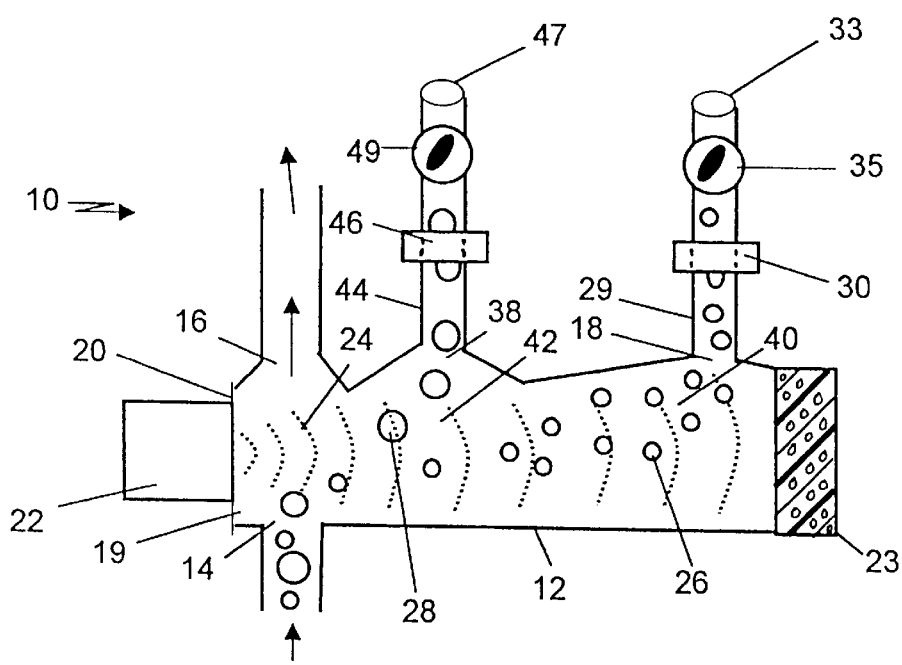
FIG. 2 is a vertical section, partly in schematic form, of a second embodiment of the invention.

FIG. 2 depicts an alternative embodiment which takes advantage of the fact that small bubbles 26 are deflected more strongly than the larger bubbles 28. In that embodiment, a center outlet 38 is added to the top of chamber 12 between the main outlet 16 and the secondary outlet 18. The upper walls of the chamber 12 are inclined adjacent the outlets 18 and 38 so as to direct bubbles from the areas 40 and 42, respectively, into the outlets 18 and 38. By adjusting the power output of the transducer 22, the system 10 can be so tuned that small microemboli 26 are diverted through the outlet 18, while large microemboli 28 are diverted through the central outlet 38 into the stasis column 44. By positioning a second detector 46 adjacent the column 44, the system 10 can measure bubble sizes and counts more accurately because small bubbles will not be masked by large ones, and the detectors 30 and 46 can each be more finely tuned within a smaller range of bubble sizes. Air accumulating in column 44 can be vented to vent 47 by opening stopcock 49.

It should be noted that the ultrasonic energy of transducer 22 is effective in diverting microair bubbles, but does not divert liquid or solid substances such as small blood clots or bone chips. The reason for this is that acoustic pressure is a function of scatter, and scatter is greatest near the resonant frequency of an air bubble. Consequently, the relative diversion force applied to air bubbles of varying sizes can be adjusted by varying the frequency of the ultrasonic energy.

It is understood that the exemplary ultrasonic diversion of microair in blood described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

We claim:

1. An ultrasonic microair filter for heart-lung machines or the like, comprising:
   a) a blood flow path having a blood stream flowing therethrough, said bloodstream carrying microair bubbles therein;
   b) a diversion chamber interposed in said blood path;
   c) at least one stasis column, said diversion chamber communicating with said stasis column at a point laterally spaced from said blood path; and
   d) a transducer so acoustically connected to said diversion chamber as to radiate acoustic energy through said diversion chamber in a direction transverse to said bloodstream and toward said stasis column;
   e) said acoustic energy being of a power level and frequency sufficient to push said microair bubbles out of said bloodstream into said stasis column.

2. The filter of claim 1, further comprising:
   f) a bubble counter so positioned with respect to said stasis column as to provide a count of the microair bubbles rising through said stasis column.

3. The filter of claim 1, in which said stasis column includes a stopcock allowing air accumulated in said stasis column to be selectively vented.

4. An ultrasonic microair filter for heart-lung machines or the like, comprising:
   a) a blood flow path having a bloodstream flowing therethrough, said bloodstream carrying microair bubbles therein;
   b) a diversion chamber interposed in said blood path;
   c) at least one stasis column, said diversion chamber communicating with said stasis column at a point laterally spaced from said blood path; and
   d) a transducer so acoustically connected to said diversion chamber as to radiate acoustic energy through said diversion chamber in a direction transverse to said bloodstream and toward said stasis column;
   e) said acoustic energy being of a power level and frequency sufficient to push said microair bubbles out of said bloodstream into said stasis column;
   f) said filter having a plurality of stasis columns spaced from one another in a direction transverse to said bloodstream, said acoustic power level and frequency being such that bubbles of a first predetermined range of sizes are diverted into one of said stasis columns, and bubbles of another predetermined size range are diverted into another of said static columns.

5. The filter of claim 1, in which the end of said diversion chamber upon which said radiated acoustic energy impinges is formed of a biocompatible acoustic damping foam.

6. The filter of claim 1, in which said power level is substantially 20 W, and said frequency is substantially 1 MHz.

* * * * *